United States Patent [19]
Linehan et al.

[11] Patent Number: 5,469,061
[45] Date of Patent: Nov. 21, 1995

[54] SPECTROMETER CAPILLARY VESSEL AND METHOD OF MAKING SAME

[75] Inventors: John C. Linehan, Richland; Clement R. Yonker, Kennewick; Thomas S. Zemanian, Richland; James A. Franz, Kennewick, all of Wash.

[73] Assignee: Battelle Memorial Institute, Richland, Wash.

[21] Appl. No.: 42,351

[22] Filed: Apr. 2, 1993

[51] Int. Cl.[6] ............................................. G01V 3/00
[52] U.S. Cl. .............................. 324/321; 324/300
[58] Field of Search ................................ 324/321, 318, 324/309, 307, 300; 62/511; 138/DIG. 2

[56] References Cited

U.S. PATENT DOCUMENTS

| | | | |
|---|---|---|---|
| 3,048,021 | 8/1962 | Coles et al. | 62/511 |
| 3,967,489 | 7/1976 | Pohl et al. | 62/511 |
| 4,418,546 | 12/1983 | Buswell | 62/511 |
| 4,927,265 | 5/1990 | Brownlee | 356/73 |
| 5,313,162 | 5/1994 | De Graaf et al. | 324/318 |

OTHER PUBLICATIONS

"High-temperature NMR probe" by T. S. Aurora et al. Rev. Sci. Instrum. 53(8) Aug. 1982.
"An Inexpensive Coaxial NMR Cell" by J. F. Hinton et al. Jour. of Chem. Education, vol. 43 No. 8 Aug. 1966 p. 443.
"A Convenient NMR External Standard Tubing" by Chang et al. Applied Spectroscopy vol. 28 No. 2, 1974 pp. 201 (Month of publication unknown).
Glass Capillary for High Resolution NMR Measurements at Pressures up to 400 MPa, R. K. Williams, Rev. Sci. Instrum. 49(5), May 1978.
Some Aspects of High-Pressure NMR, I. Ando, G. A. Webb, Magnetic Resonance in Chemistry, vol. 24, 557–567, (1068) Apr. 1986.
Pressure-Resisting Glass Cell for High Pressure, High Resolution NMR Measurement, H. Yamada, Rev. Sci. Instrum. vol. 45, No. 5, May 1974.
Nuclear Magnetic Resonance and Laser Scattering Techniques at High Pressure, J. Jones, High Pressure Chemistry and Biochemistry, 193–235, 1987 (Month of pub. unknown).

*Primary Examiner*—Louis Arana
*Attorney, Agent, or Firm*—Paul W. Zimmerman

[57] ABSTRACT

The present invention is an arrangement of a glass capillary tube for use in spectroscopy. In particular, the invention is a capillary arranged in a manner permitting a plurality or multiplicity of passes of a sample material through a spectroscopic measurement zone. In a preferred embodiment, the multi-pass capillary is insertable within a standard NMR sample tube. The present invention further includes a method of making the multi-pass capillary tube and an apparatus for spinning the tube.

16 Claims, 9 Drawing Sheets

SPECTROMETER CAPILLARY VESSEL AND METHOD OF MAKING SAME

This invention was made with Government support under Contract DE-AC06-76RLO 1830 awarded by the U.S. Department of Energy. The Government has certain rights in the invention.

FIELD OF THE INVENTION

The present invention relates generally to a capillary vessel used for containing a material sample for spectroscopy, and a method for making the capillary vessel. More specifically, the present invention discloses a capillary vessel having a plurality of passes through a measurement zone within a spectrometer bore. The vessel is made by shaping a capillary tube.

BACKGROUND OF THE INVENTION

Nuclear magnetic resonance (NMR) spectroscopy is performed by exposing a material sample to a magnetic field. Material samples are generally liquid but can also be gaseous or solid. The sample is placed within a sample tube that is placed in the magnetic field. The nuclear spins of the atoms within the material sample come into an equilibrium in the presence of the magnetic field which aligns the nuclear spins of atoms within the material sample. After alignment, the material sample is exposed to electromagnetic energy having a radio frequency that perturbs the nuclear spins of the atoms from their equilibrium. As the perturbed nuclear spins return to equilibrium, energy in the form of a second electromagnetic radio frequency unique to the environment of the atoms is observed and measured.

NMR is used for research to study chemical behavior of many compounds. Because compounds behave differently at different conditions of temperature and pressure, it is necessary to perform NMR spectroscopy at different conditions to obtain a thorough understanding of the chemical behavior of a particular compound over a wide range of conditions.

However, performing tests at high pressures, particularly as high as 4 kbar and above, using NMR is difficult. The vessel containing the material sample must be non-magnetic and must have sufficient mechanical strength to withstand the stress induced by the internal pressure.

This problem has been recognized and various approaches taken. In an article *NUCLEAR MAGNETIC RESONANCE AND LASER SCATTERING TECHNIQUES AT HIGH PRESSURE*, Jiri Jonas, *High Pressure Chemistry and Biochemistry*, pp. 193–235, 1987, several devices for achieving high pressure NMR spectroscopy are disclosed. Pressures ranging from 0.062 kbar to 9 kbar are achieved with the devices shown in FIGS. 4, 5, and 6 of Jonas. These devices have two common characteristics. First, they are straight, once-through vessels, and second, they are custom designed for a particular spectrographic measurement and are neither interchangeable nor broadly useful for a variety of measurements.

Another article, *PRESSURE-RESISTING GLASS CELL FOR HIGH-PRESSURE, HIGH-RESOLUTION NMR MEASUREMENT*, Hiroaki Yamada, *Rev. Sci. Instrum.*, Vol. 45, No. 5, May 1974, discloses achievement of test pressures up to about 2 kbar with a glass capillary vessel. Further disclosed are the details of construction of the once-through capillary and connection to a standard high pressure tube.

A third article, *SOME ASPECTS OF HIGH-PRESSURE NMR*, I Ando and G. A. Webb, *Magnetic Resonance in Chemistry*, Vol 24, pp. 557–567 (1986) discusses the use of non-magnetic materials for NMR vessels, in particular, metals including stainless steel, beryllium copper alloy and titanium alloy, and glass in the form of glass capillary.

A fourth article, *GLASS CAPILLARY FOR HIGH RESOLUTION NMR MEASUREMENTS AT PRESSURES UP TO 400 MPa*, R. K. Williams, *Rev. Sci. Instrum.* 49(5), May 1978, discloses use of Pyrex glass tubing cleaned in hydrogen fluoride then drawn to form a capillary vessel.

While there are many embodiments of NMR sample vessels having high pressure capability, each one is uniquely designed for spectroscopy of a particular material or to obtain a particular spectroscopic result and are not interchangeable. All of the designs have limited sample volume, thereby limiting the spectroscopic measurements that may be performed. Some designs prohibit the technique of spinning the sample to obtain greater line-width resolution.

Sample vessels made of glass or other brittle materials, for example sapphire, fail catastrophically, thereby potentially damaging equipment and/or injuring personnel. Copper-beryllium alloy is expensive and difficult to machine because of toxicity and hardness of the alloy.

It is therefore desirable to those skilled in the art of NMR measurements to have an NMR sample vessel capable of withstanding high pressure and having the capability of providing a variety of NMR spectrographic measurements. It is further desirable to have such a vessel for other types of spectrometry, for example electron spin resonance spectroscopy (ESR), where measurements at high pressure are desired.

SUMMARY OF THE INVENTION

The present invention is an arrangement of a glass capillary tube as a sample vessel for use in spectroscopy. In particular, the invention is a capillary arranged in a manner permitting a plurality or multiplicity of passes of a sample material through a spectrometer measurement zone. The sample vessel may be stationary or spun within the measurement zone. In a preferred embodiment, the multi-pass capillary is insertable within standard sample tubes, for example, standard NMR probes. Advantages of the present invention include: the multi-pass sample tube fails benignly, has greater sample volume than a single-pass capillary tube, and thereby provides a greater variety of measurement results with a single NMR sample tube. More particularly, it permits obtaining high sensitivity spinning and non-spinning NMR spectra of any nucleus, including protons. In addition, the present invention permits the use of nucleus, for example proton, decoupling. Moreover, numerous NMR pulse techniques, including but not limited to Attached Proton Test (APT), Heteronuclear Correlation Spectroscopy (HETCOR) and Homonuclear Correlation Spectroscopy (HOMCOR), may be utilized without modification to an NMR spectrometer.

The subject matter of the present invention is particularly pointed out and distinctly claimed in the concluding portion of this specification. However, both the organization and method of operation, together with further advantages and objects thereof, may best be understood by reference to the following description taken in connection with accompanying drawings wherein like reference characters refer to like elements.

DESCRIPTION OF THE PREFERRED EMBODIMENT(S)

Figure 1:
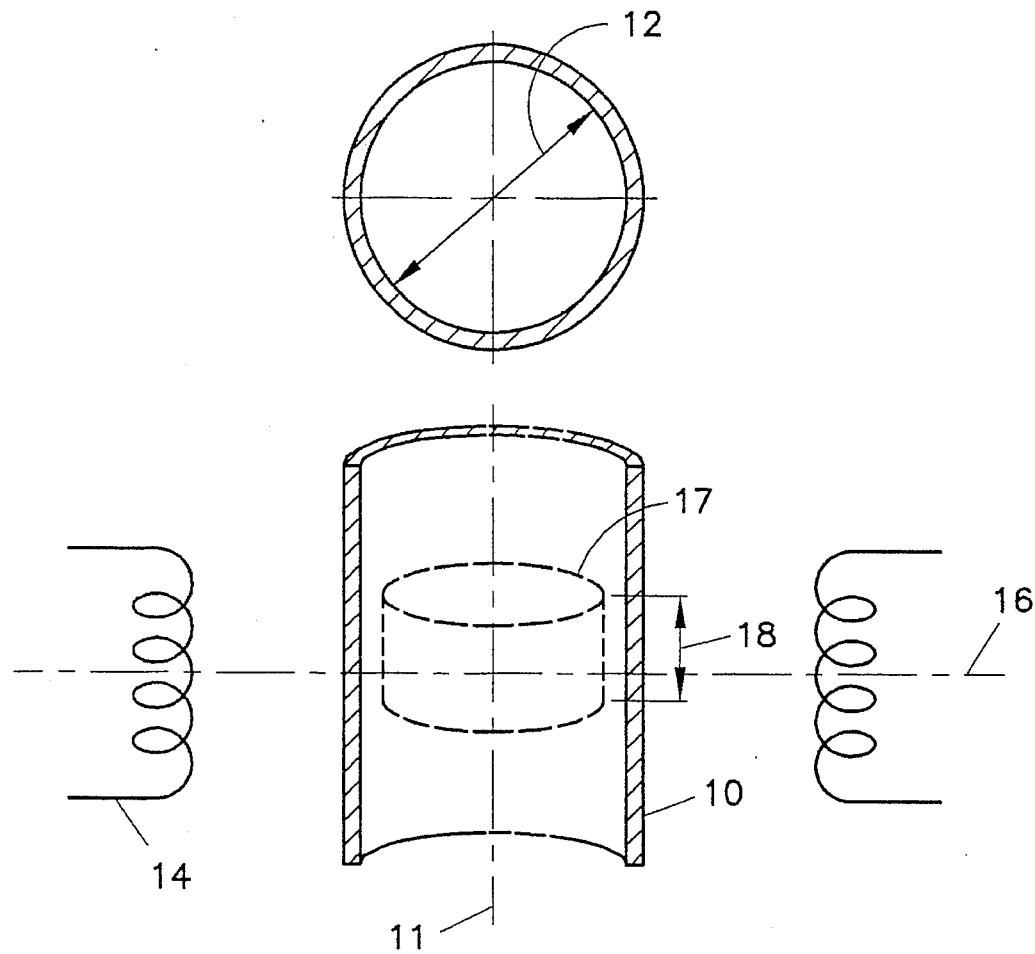
FIG. 1 is a diagram of an NMR instrument.

In an NMR instrument as depicted, for example, in FIG. 1 (prior art), the instrument is usually constructed with a material sample tube bore (10) having a longitudinal axis (11) and inside diameter (12). A magnetic coil (14) having a magnetic coil axis (16) is placed around the material sample tube bore (10). The longitudinal axis (11) is generally oriented perpendicular to the magnetic coil axis (16) but may have alternative orientations. While the magnetic field is present all around the instrument, there is created a measurement zone (17) having a length (18) within the material sample tube bore (10) wherein spectroscopy of a material sample occurs. For best resolution and pertinent test results, it is preferred to minimize the material sample variables within the measurement zone (17).

Figure 2:
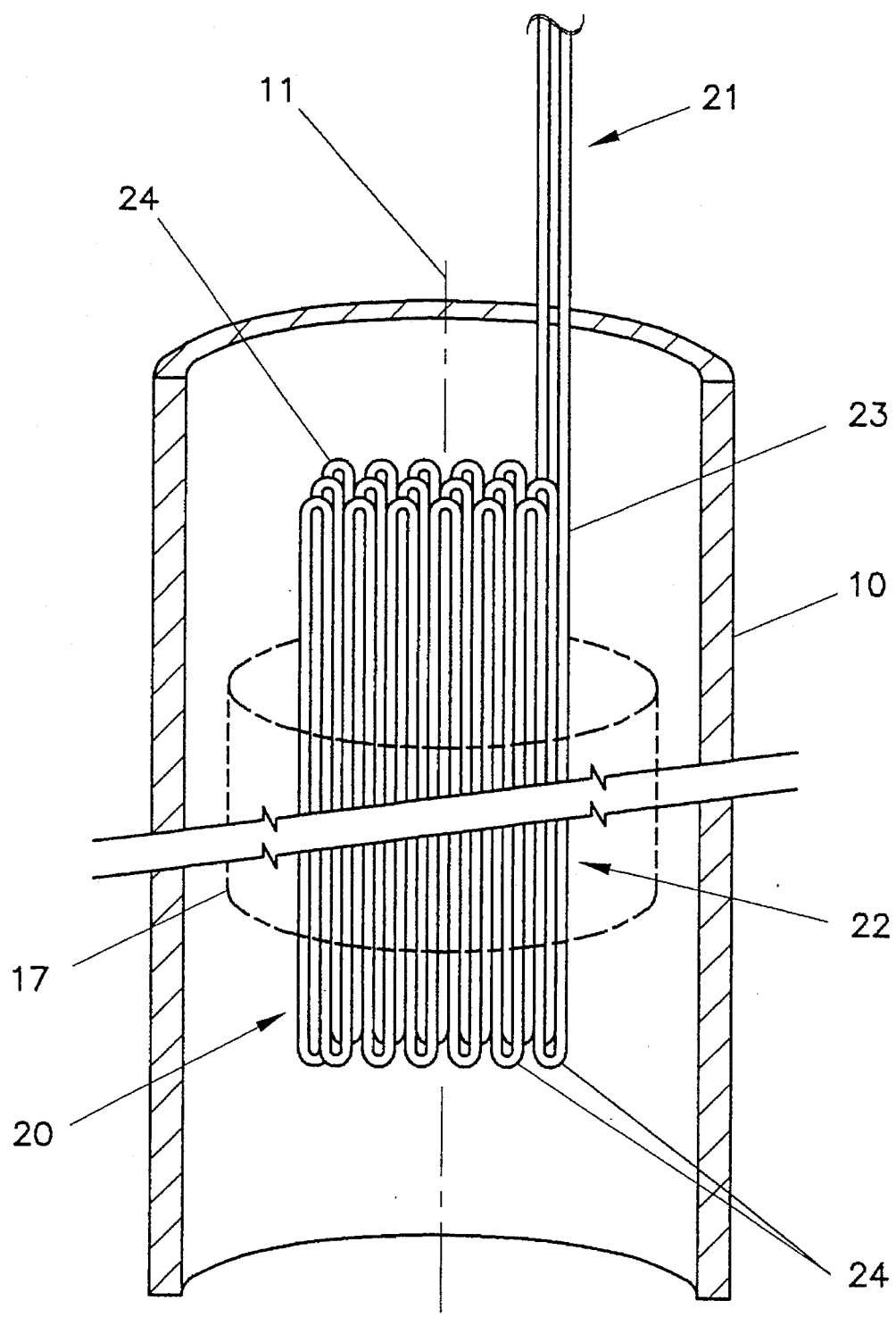
FIG. 2 is an isometric sketch of a preferred embodiment of the present invention.

Consistent with variable minimization within the measurement zone (17) and permitting NMR spectroscopy at high pressure with large sample volume, in FIG. 2 the material sample vessel (20) is a capillary tube (21) bent into a plurality of passes (22). The number of passes (22) is limited by the diameter (12) of the sample tube bore (10) and the length (18) of the measurement zone (17). In FIG. 2, each pass (22) comprises a longitudinal section (23) and at least one reversing bend (24). The length of the longitudinal passes (22) is sufficient to place the reversing bends (24) outside the measurement zone (17). By placing the reversing bends (24) outside the measurement zone (17), the geometry of the passes (22) is similar to each other within the measurement zone (17).

Figure 3:
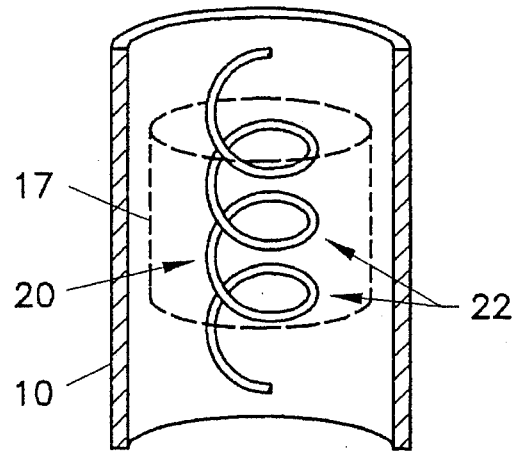
FIG. 3 is an isometric sketch of a second preferred embodiment of the present invention.

Use of passes (22) is not limited to straight vertical longitudinal sections (23) having reversing bends (24) as shown in FIG. 2. In FIG. 3, passes (22) are coils of a helix. The passes (22) of FIGS. 2 and 3 are not limited to vertical orientation or symmetry. They may be placed horizontally or at various angles. In addition, there may be provision for spinning the passes (22) about an axis of orientation. Passes (22) are not limited to straight sections or continuously curved sections and may include zigzag or yarn-ball configurations. As indicated above, some configurations are less preferred; for example, the yarn-ball configuration is less preferred because of the random orientation of passes (22) within the measurement zone (17).

Figure 4:
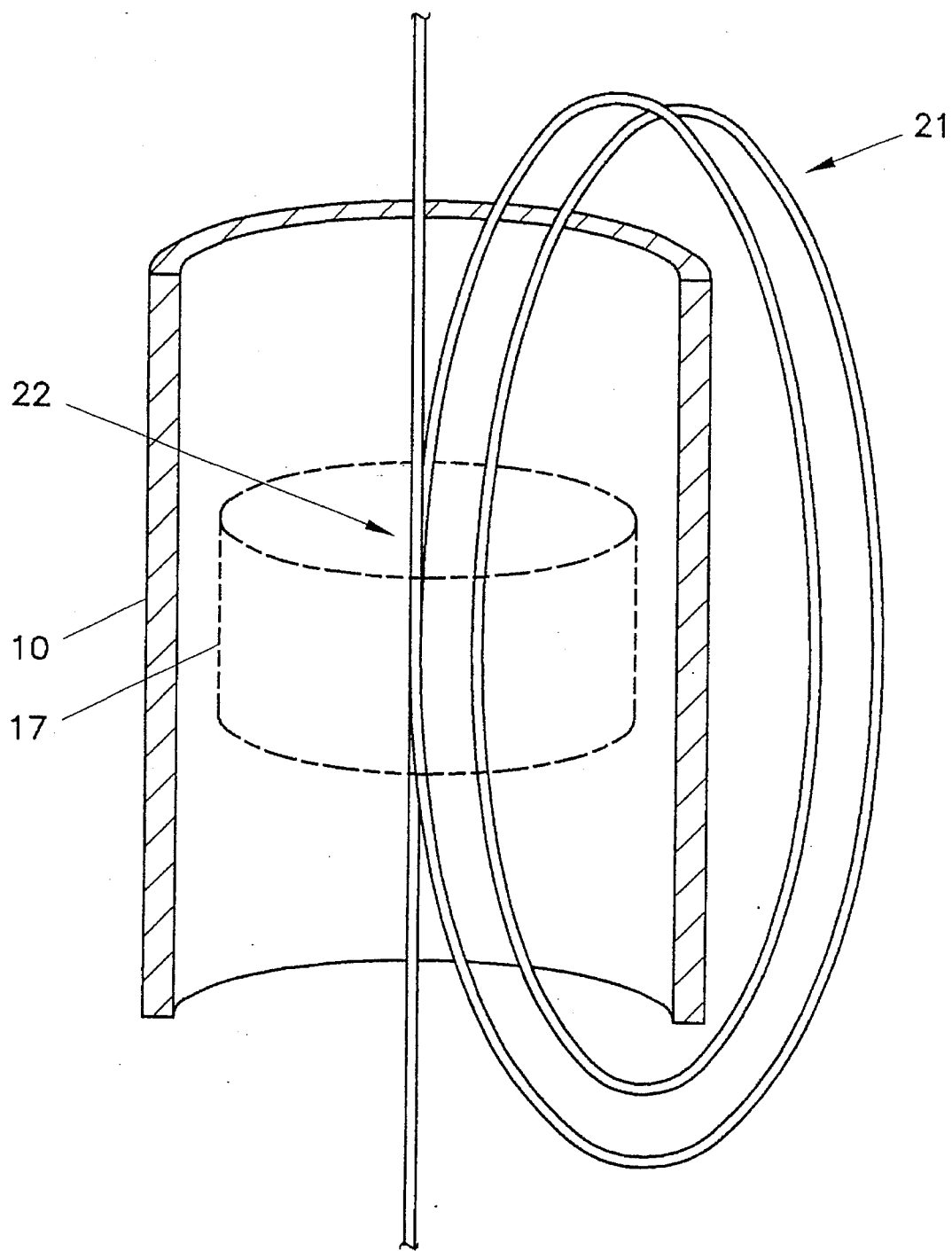
FIG. 4 is an isometric sketch of a third preferred embodiment of the present invention.

Multiple passes (22) may be accomplished, according to FIG. 4, by looping capillary tubing (21) through the bore (10). This embodiment is less preferred because it requires the tube bore (10) to be open ended and it further requires additional capillary tubing (21) and sample material. However, it may be preferred for flow through measurements.

A capillary tube is selected for its mechanical resistance to high pressure. The capillary may be of any non-magnetic material, but it is preferred to use fused silica glass capillary for its modest cost, high strength, optical purity and ease of manipulation into various desired passes (22). It is further preferred that the capillary have a first polymer coating, for example polyimide. It is further preferred that a second coating, for example a polyester resin, be applied to the material sample vessel (20) for containing glass shards in the event of failure of the capillary tube.

Because manipulation of the glass requires heating to a glass softening temperature that is higher than the decomposition temperature of the polymer coating, the polymer coating will be burned off heated sections. After shaping and cooling the sample vessel (20), an organic coating, for example cyanoacrylate, may be applied to restore a coating to the heated sections. Cyanoacrylate is preferred as a coating because it has a low viscosity and it has good adhesion.

Figure 5:
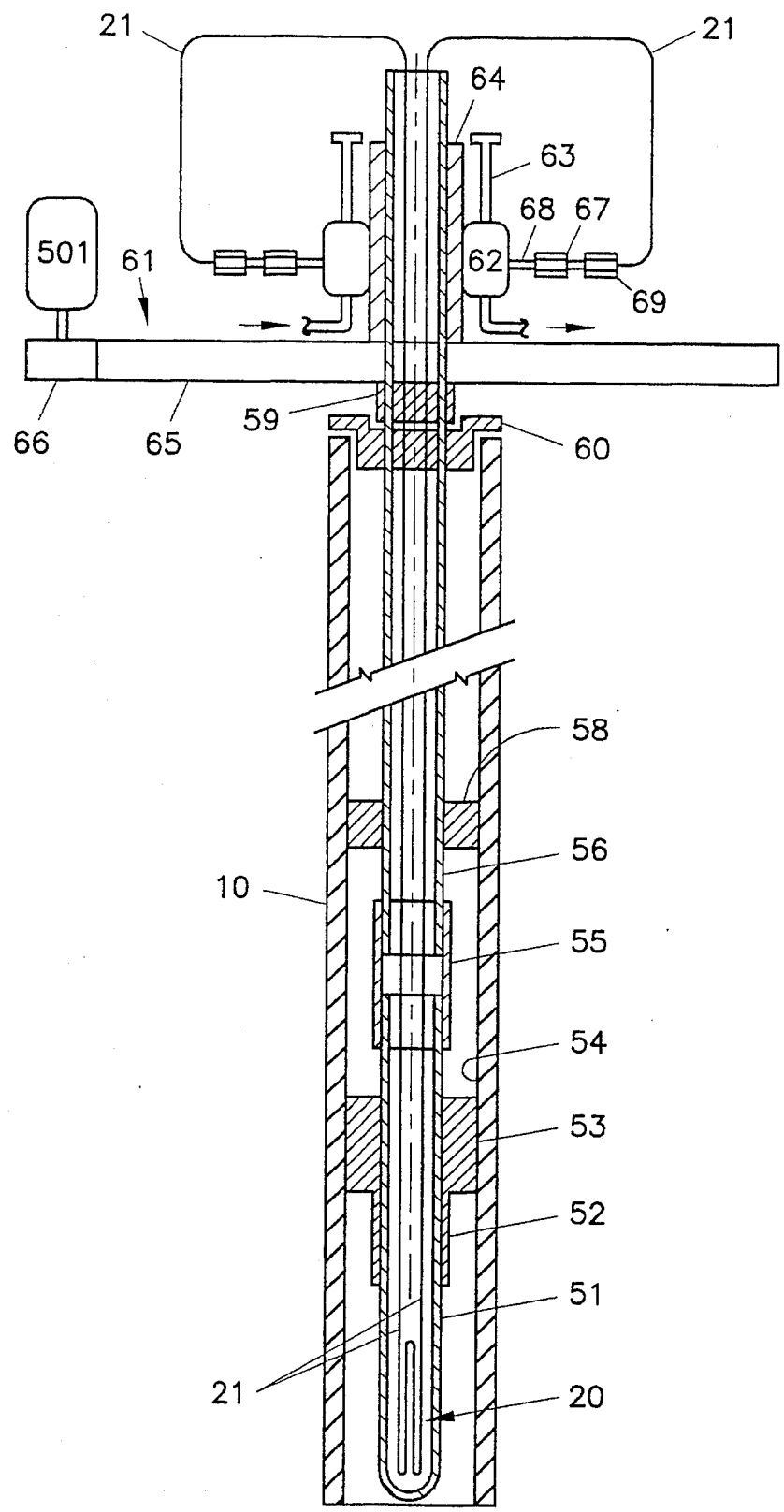
FIG. 5 is a cut-away of a spinning apparatus.

For certain measurement results, particularly enhanced resolution in NMR measurements, it is beneficial to rotate the material sample vessel (20) about an axis, for example the longitudinal axis (11), a technique referred to by those skilled in the art as 'spinning'. Spinning of the sample vessel (20) may be accomplished with the apparatus shown in FIG. 5.

The material sample vessel (20) is placed within a standard sample tube (51) with both material sample vessel (20) and spectrometer tube (51) extending through a standard spinner (52) having a surface (53) slideably bearing on an inner surface (54) of bore (10). The spinner (52) further permits stroboscopic measurement of spin rate.

A sleeve coupling (55) joins the spectrometer tube (51) to a standard tube (56). The standard tube (56) is supported within the bore (10) with bearings (58 and 59). Although bearing (58) is shown above the sleeve coupling (55), it will be apparent to those skilled in the art of mechanical spinner design that bearing (58) could also be placed between the sleeve coupling (55) and the spinner (52). A support ring (60) rests on tube bore (10) and supports bearing (59). Rotation means (61) provides the motive power for spinning. Material sample valves (62) permit filling of the material sample vessel (20) then disconnecting of the material sample source (not shown), thereby permitting rotation of the material sample vessel (20).

The sample valves (62) are standard high-pressure valves modified by removing the stem handle and replacing it with a headed bolt (63) to avoid hitting and breaking the standard tube (56) extending between the sample valves (62). For mechanical stability, a spacer (64) may be placed between the sample valves (62) that permits extension of and protects the standard tube (56). It is preferred that the headed bolts (63) and the spacer (64) be of non-magnetic material.

The headed bolts (63) may be of any type, wrench driven or screwdriver driven, but it is preferred to use wrench-driven hex head bolts.

The capillary tube (21) is connected to the sample valves (62) through a tubing coupling (66). While any high pressure tubing coupling is operable, it is preferred to use 1/16-inch ferruled coupling. The tubing coupling has a first end (67) connected to tubing (68) and a second end (69) having a ferrule (not shown). The ferrule may be of any material but is preferably Vespel. The ferrule is pre-drilled with a drill of slightly larger diameter than the outside diameter of the capillary tube (21). The capillary tube (21) is inserted into the pre-drilled ferrule. Tightening of a coupling on the second end (69) causes the ferrule to bear against the capillary thereby sealing the ferrule and capillary. This arrangement is viable for pressures up to about 1 kBar, above which the capillary is forced longitudinally out of the ferrule. Addition of cyanoacrylate before tightening permits it to flow between the ferrule and the capillary. The coupling is tightened prior to drying of the cyanoacrylate. After the cyanoacrylate is dry, the connection is useful for pressures up to about 4 kBar.

The rotation means (61) may be any means including but not limited to steam, pneumatic, electric, and manual rotation means. In a preferred embodiment, the spectrometer tube (51) is attached to a follower wheel (65), preferably through the spacer (64) that is attached to the follower wheel (65). A driving wheel (66) powered by an electric motor (501) provides the motive power for spinning. The wheels (65, 66) may be any positive traction wheel combination, but are preferably gears, and more preferably plastic gears.

Figure 6A:
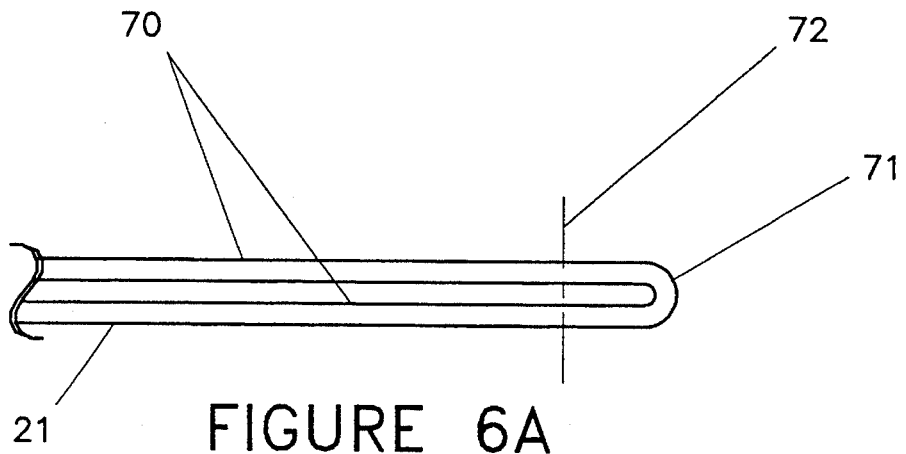
FIG. 6a is an isometric of a two-pass capillary.
Figure 6B:
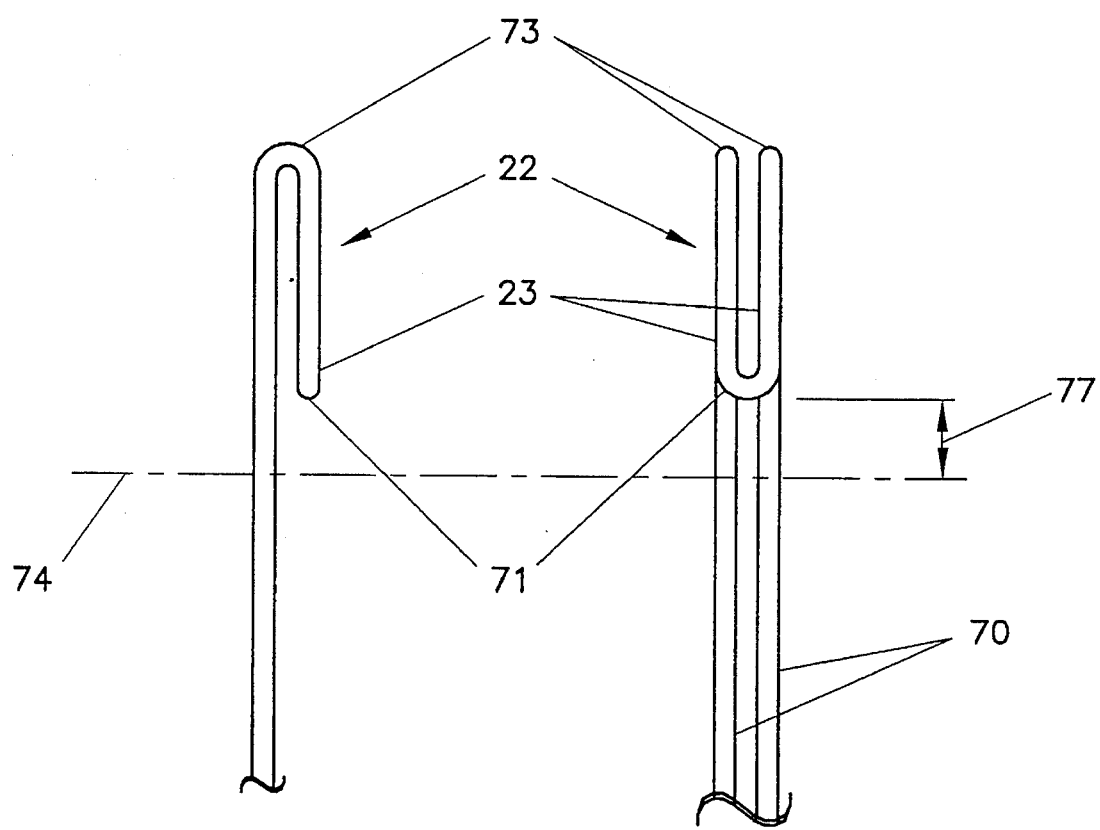
FIG. 6b is an isometric of a four-pass capillary.
Figure 6C:
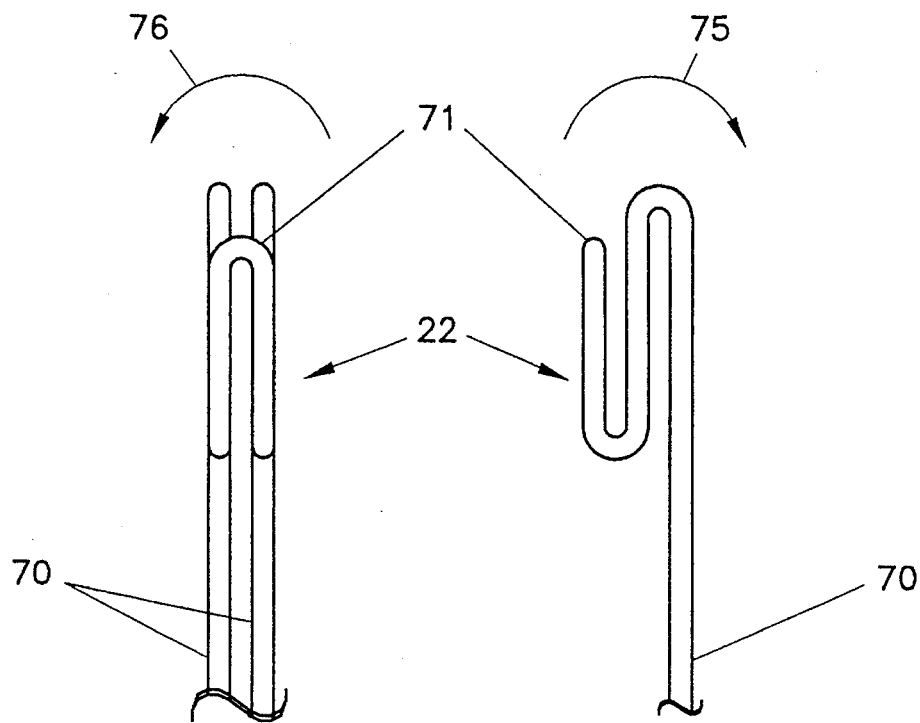
FIG. 6c is an isometric of a six-pass capillary.

Construction of the material sample vessel (20) is accomplished by the following steps taken in reference to FIGS. 6a, 6b and 6c. A length of glass capillary tube (21) is bent into a hairpin or "U" shape as shown in FIG. 6a having two lengths of capillary (70) and a reverse bend (71). Bending is accomplished by heating with a pencil-tip torch, for example Microflame, available from Radio Shack retail stores. At a first location (72) the two lengths (70) are heated with the pencil tip torch and as the heated location (72) softens, the end having the reverse bend (71) is permitted to fall under its own weight and the entire "U" shape positioned so that the capillary (21) is folded, forming reverse bends (73) and longitudinal sections (23) as shown in FIG. 6b. Gentle pressure is applied transversely to the longitudinal sections to place the passes (22) as close together as practicable. The gentle pressure may be applied by means including but not limited to hand pressure. Heating is continued during application of transverse pressure so that the reverse bends are pliable during application of the gentle transverse pressure.

At a second location (74) the two capillary lengths (70) are heated and folded to obtain the shape shown in FIG. 6c. Further folds are made by heating and bending transverse to a plane defined by the two lengths (70) in a first fold direction (75). Additionally, further folds are made by heating and bending within a plane defined by the two lengths (70) in a second fold direction (76). Oblique folds in directions between the first fold direction (75) and the second fold direction (76) are also made. The direction of folding is selected to minimize spacing between passes (22).

It is important to avoid overheating the capillary tube (21) and to avoid pinching the capillary while bending so that the inner diameter is not closed and remains open to freely pass sample material. Hence, upon heating a location of capillary after having made one or more folds, for example the second location (74), it is preferable that the second location (74) is a distance (77) from previously formed reverse bend (71) to avoid reheating reverse bend (71).

Upon having made as many passes (22) as desired, it is preferred to place a band around the material sample tube (20) in order to hold the passes (22) together while coating the reverse bends (24, 71). Use of a band improves repeatability of fitting within a sample tube bore (10) compared to not using a band. The band may be of any material having flexibility and modest tensile strength, and it is preferred that the material be non-magnetic. Materials for the band include but not limited to polytetrafluorethylene (PTFE) tape, non-magnetic wire, rubber bands, adhesive tape, glass tubing, and sections of NMR tubing.

The heating and folding may be done with a single length of capillary tube (21) or with more than two premade lengths (70). It is less preferable to use a single length because the number of folds is doubled to obtain the same size material sample vessel (20), and handling a long single length either on a spool or on a bench is cumbersome compared to handling and manipulating the premade lengths (70). It is less preferable to use more than two premade lengths (70) because the pencil tip torch tip cannot heat more than two premade lengths (70) simultaneously. If the torch were fitted with a tip capable of making a line of flame, then more than two premade lengths (70) would be heatable simultaneously.

EXAMPLE 1

An experiment was conducted to determine whether fused silica glass capillary would provide suitable NMR spectrographic measurements. Specifically, the experiment was to determine whether the glass capillary either (a) introduced any new output signal or (b) shielded or shifted any output signal.

Figure 7:
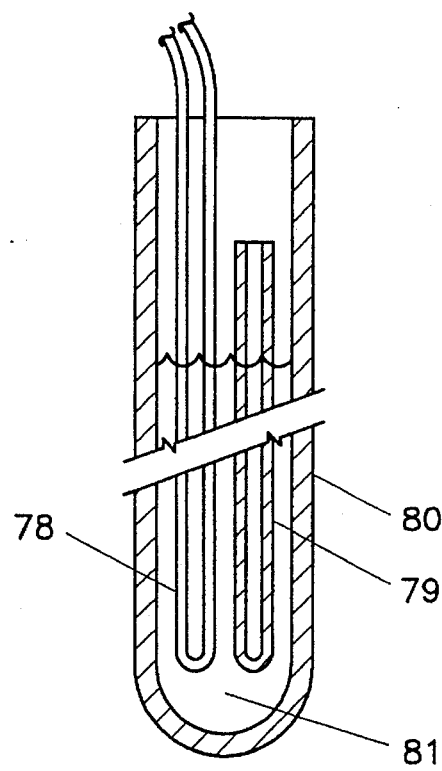
FIG. 7 is a cut-away of experimental equipment.

For this experiment, three compounds were placed in an NMR sample tube according to FIG. 7. A two-pass fused silica capillary (78) was filled with methylene chloride. The two-pass fused silica capillary was made from a straight fused silica capillary tube having an outside diameter of 360 micrometers and an inside diameter of 100 micrometers, and having a polyimide coating of a thickness of about 19 micrometers. A section of the straight capillary was heated with a pencil-tip butane/$NO_x$ flame torch and the heated section bent to form a reverse bend (71) with longitudinal sections (70) according to FIG. 6a. The fused silica capillary was cooled then painted with cyanoacrylate to restore a coating to the heated section.

A melting point tube (79) of borosilicate glass was filled with deuterated trichloromethane. Both the filled fused silica two-pass capillary (78) and the filled melting point tube (79) were placed within an NMR sample tube (80) and the remaining volume (81) within the NMR sample tube (80) was filled with deuterated water.

The filled NMR sample tube (80) was placed in an NMR spectrometer and a calibration was performed using the deuterated trichloromethane as the internal reference. The chemical shift (ppm) of the deuterated trichloromethane was set to a value of 7.24 as may be found in *The Aldrich Library of NMR Spectra*, Vol. 1, Chas. J. Pouchert and J. R. Campbell, Aldrich Chem. Co., 1974.

Figure 8:
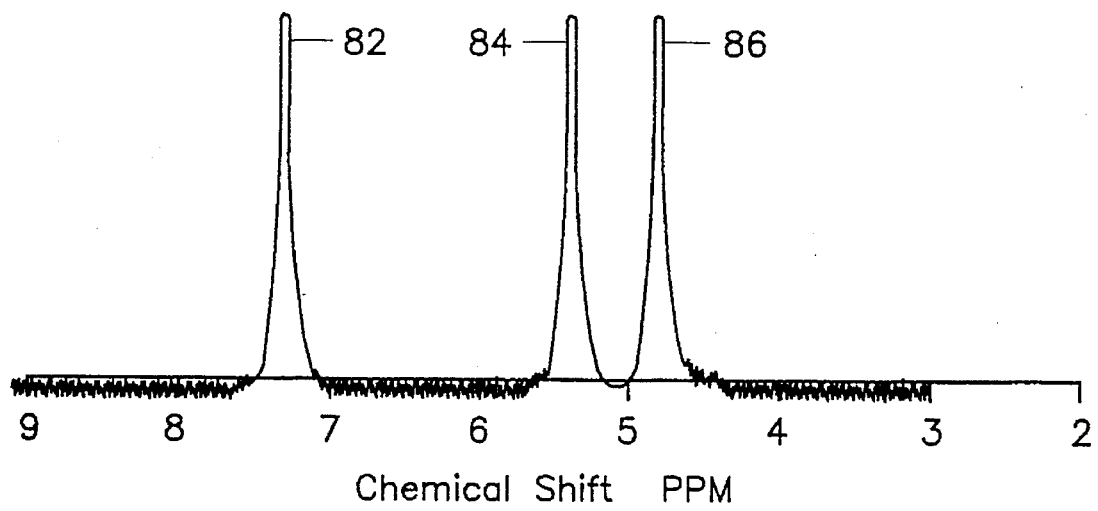
FIG. 8 is an NMR spectrograph.

Results of the subsequent measurements are shown in FIG. 8 and summarized in the following Table. FIG. 8 shows three distinct peaks (82, 84, and 86) corresponding to deuterated trichloromethane, methylene chloride and deuterated water respectively. The lack of any other peaks indicates that the fused silica capillary added no additional signal to the measurement.

| Example 1 NMR Results | | |
| --- | --- | --- |
| Compound | Measured Chemical Shift (ppm) | Expected Chemical Shift (ppm) |
| d-trichloromethane | 7.24A | 7.24A |
| Methylene Chloride | 5.30 | 5.32 |
| d-water | 4.85 | 4.63 |

The measured chemical shift of methylene chloride is well within experimental error of the expected value from The Aldrich Chemical Library of NMR Spectra. Because the methylene chloride was within the fused silica capillary, these results show that the fused silica capillary did not shield or shift the methylene chloride signal.

The measured chemical shift of the deuterated water is also within acceptable experimental error of the expected literature value. The larger variation in the deuterated water signal compared to the methylene chloride may be attributed to variation in pH, which was not controlled for this experiment.

EXAMPLE 2

Two experiments were conducted using a multi-pass material sample tube (20) as shown in FIG. 2. The material sample tube was made according to the procedure of Example 1 with the additional step of heating with a pencil-tip butane/$NO_x$ flame torch at locations spaced apart about 40 millimeters, and the heated sections bent to form reverse bends (73) with longitudinal sections (23) therebetween according to FIG. 2 and FIGS. 6b and 6c. The multi-pass material sample tube (20) was cooled then painted with cyanoacrylate to restore a coating to the heated sections. The multi-pass material sample tube (20) was inserted into a standard sample tube (51) for NMR having a nominal diameter of 5 mm. Deuterated water (D20) was then placed within the standard NMR tube (51) displacing the ambient gas (air) and filling the volume between the passes (22) of the multi-pass material sample tube (20) and the standard sample tube (51). The deuterated water provides a lock signal and a reference signal for the NMR spectrometer.

The completed sample tube containing the multi-pass material sample tube and the deuterated water was placed within a sample bore (10) of an NMR spectrometer and the multi-pass material sample tube was filled with ethylene. The ethylene was pressurized up to 3 kbar and proton NMR spectrographic measurements taken.

Figure 9A:
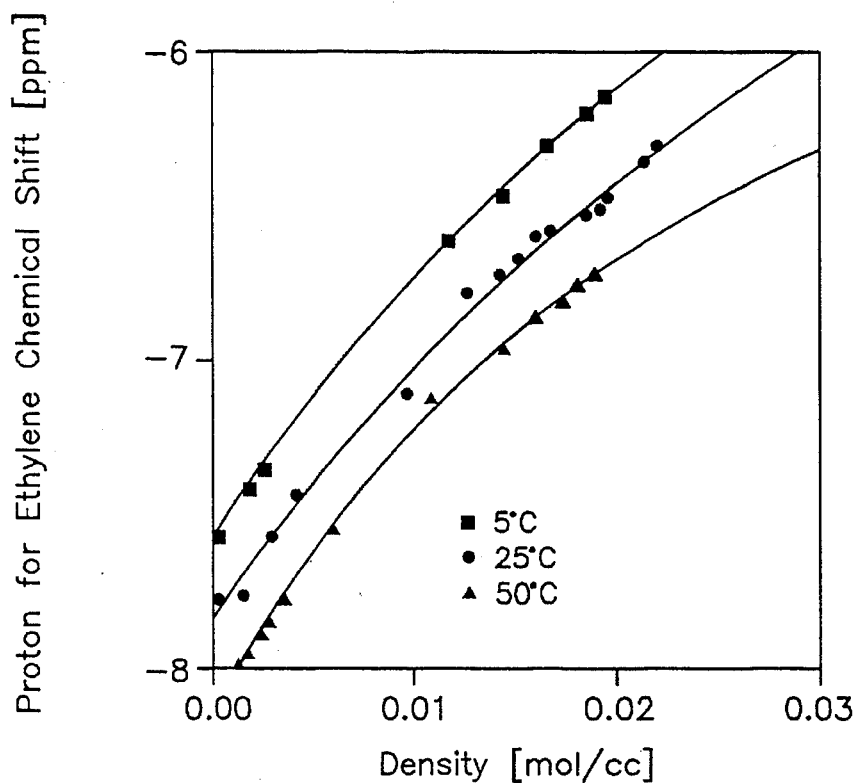
FIG. 9a is a graph showing chemical shift of ethylene.

The results of the proton NMR spectrographic measurements at various temperatures are shown in FIG. 9a. The 25 C isotherm data were obtained at pressures up to 3 kbar while the 5 C and 50 C isotherm data were obtained at pressures up to 1 kbar. Because the multi-pass material sample tube has flow-through capability, the pressure can be quickly and easily changed between measurements and between data points, resulting in obtaining an isotherm in at most about 2 days per isotherm.

A multi-pass material sample tube was again employed to obtain measurements of xenon particularly measurements near the critical point of xenon. Again, the flow-through capability of the sample tube permitted close, in-measurement control of the pressure of the sample, resulting in obtaining up to 14 data points in less than 1 day.

Figure 9B:
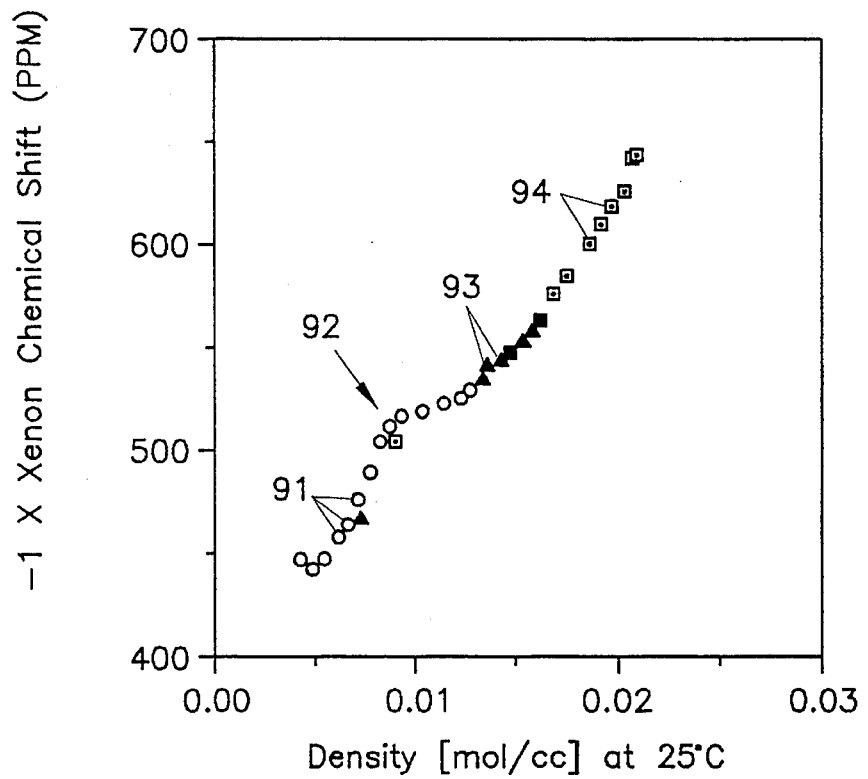
FIG. 9b is a graph showing chemical shift of xenon.

The results of the xenon measurements are shown in FIG. 9b. The critical pressure of xenon is about 846 psia. Data points (91) obtained near the critical point (92) correspond to pressure differentials of from about 20 psi to about 40 psi between data points. Data points 93 and 94 correspond to pressure differentials of from about 1000 psi to about 2000 psi between data points. The three sets of data points (91, 93, and 94) were obtained on separate days Jan. 24, 1992, Aug. 24, 1992 and Aug. 5–6, 1992, respectively. The agreement of the data points and lack of discontinuities demonstrate the repeatability of the measurements even using different multi-pass material sample tubes.

EXAMPLE 3

An experiment was conducted to demonstrate utility of the multi-pass material sample tube in obtaining electron spin resonance (ESR) spectra. Specifically, an ESR spectrum of galvinoxyl dissolved in carbon dioxide was obtained.

The multi-pass material sample tube was identical to the one as described in Example 1. In a first trial, it was found that char from the burnt polyimide coating gave an additional ESR signal. Hence, the polyimide coating was completely removed by heating the entire capillary and burning off all of the polyimide coating. The capillary was re-coated with cyanoacrylate and no additional signal was observed.

Figure 10:
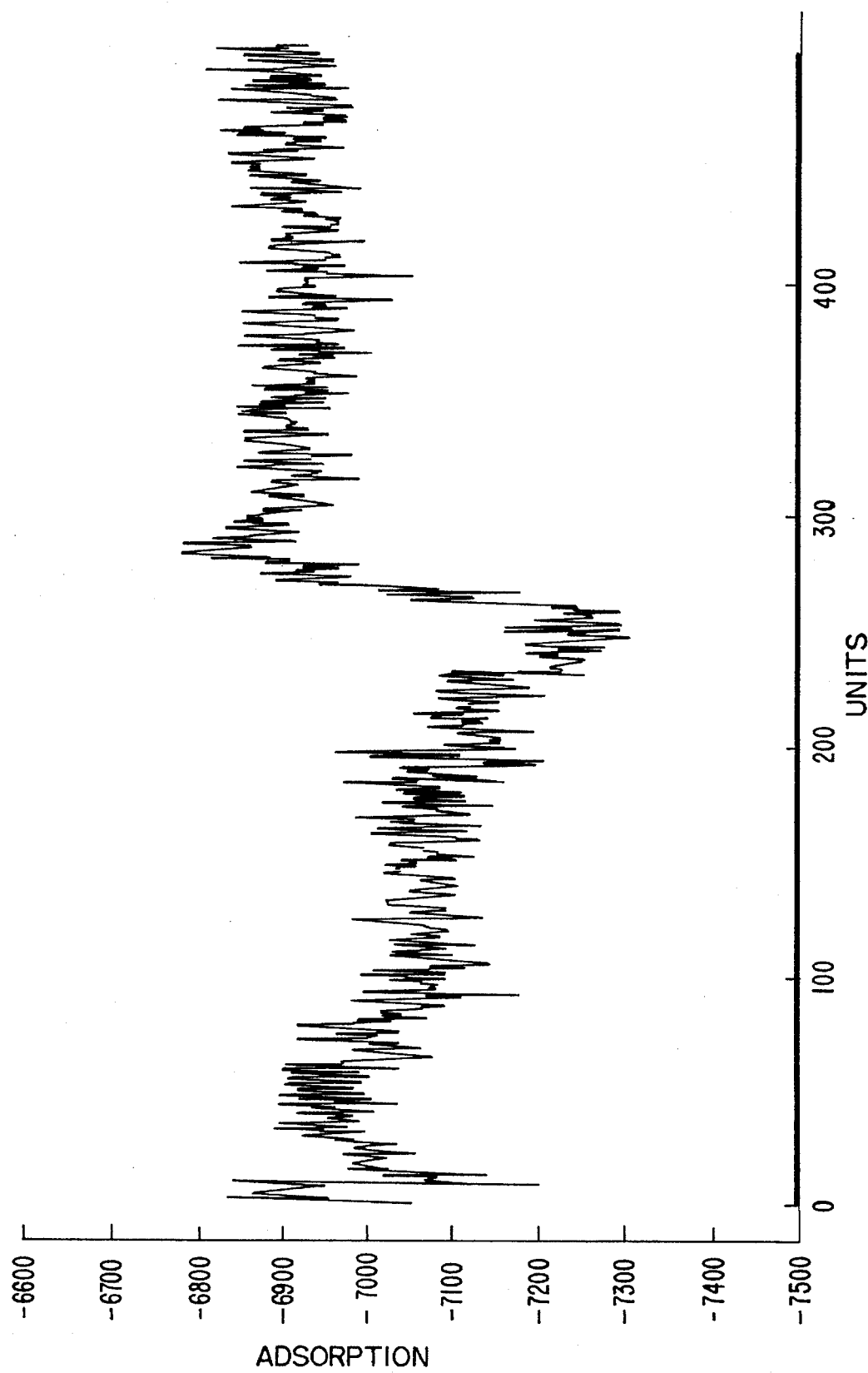
FIG. 10 is an ESR spectrum of galvinoxyl in carbon dioxide.

Results are shown in FIG. 10 showing an ESR spectrum of galvinoxyl in carbon dioxide at 1 kbar pressure.

EXAMPLE 4

After determining the operability and advantages of the multi-pass material sample tube, several spectrographic measurements were made at elevated pressures from about 5 bar to about 4 kbar. In all, about 120 measurements were made up to pressures of about 4 kbar. Out of these, there were about 7 material sample tube failures. Upon failure, the release of pressure was benign because the small inner diameter of the capillary restricted the flow of the material sample. The material sample tube was easily replaced in those instances and measurements continued without further interruption.

It was further observed that there were two modes of failure. In a first mode, the pressure forced the capillary to slide longitudinally through the ferrule until the capillary was no longer secured within the ferrule and the ferrule was open. In a second mode, the capillary broke near the ferrule. It is believed that there may be a mechanical stress riser near the ferrule either by virtue of the change in mechanical section from ferrule to capillary, or by virtue of the ferrule acting as a fixed support constraining the flexibility of the capillary, or some other stress concentration factor. Not having observed burst by over-pressure in a section of capillary away from the ferrule, the maximum operating pressure of the capillary is not known.

EXAMPLE 5

Several multi-pass material sample tubes were constructed according to Example 1, but without re-coating the heated sections. These uncoated sections containing the reverse bends were observed to fail at pressures less than 1 kbar.

ADDITIONAL EMBODIMENTS

Although the present invention has been used up to pressures of 4 kbar, it is not necessarily so limited. The pressure generation equipment was limited to 4 kbar. Hence, the ultimate operating pressure of the material sample tube itself is not presently known. Use of the present invention at lower pressures may also be desirable because of equipment and personnel safety considerations. Because the failure of a capillary is a whisper compared to failure of a larger diameter tube even at pressures as low as 0.006 kbar (100 psi), the invention is useful for pressures from atmospheric pressure to the practical mechanical limit of the coated capillary tube.

The present invention has been described in conjunction with NMR and ESR spectroscopy, but because the material sample tube is optically transparent to wavelengths greater than 170 nanometers, it may be used for optical spectroscopy, emission spectroscopy which includes fluorescence and phosphorescence spectroscopy, and Raman spectroscopy. The invention is therefore not limited to any particular spectrographic technique. The present invention may not be preferred for techniques requiring collimated or focussed beams because of anticipated additional complexity in beam focussing.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A material sample tube for a spectrometer having a measurement zone, said material sample tube, comprising:
   (a) non-magnetic material, and
   (b) said non-magnetic material sample tube having a plurality of continuous and unbroken passes through said spectrometer measurement zone.

2. A material sample tube as recited in claim 1, wherein said material sample tube is insertable within a standard sample tube.

3. A material sample tube as recited in claim 2, wherein said passes are geometrically similar to each other.

4. A material sample tube as recited in claim 3, wherein each of said passes, comprises:
   (a) a longitudinal section and
   (b) a reverse bend on at least one end of said longitudinal section.

5. A material sample tube as recited in claim 3, wherein each of said passes, comprises:
   (a) a coil.

6. A material sample tube as recited in claim 2, comprising:
   (a) fused silica capillary having an outer surface; and
   (b) a first coating on said outer surface.

7. A material sample tube as recited in claim 6, wherein said first coating is a polymer.

8. A material sample tube as recited in claim 7, wherein said polymer is polyimide.

9. A material sample tube as recited in claim 2, comprising:
   (a) fused silica capillary having an outer surface; and
   (b) an organic coating on said outer surface.

10. A material sample tube as recited in claim 9, wherein said organic coating is cyanoacrylate.

11. A material sample tube as recited in claim 2, comprising:
    (a) fused silica capillary having an outer surface;
    (b) a first coating on said outer surface; and
    (c) an organic coating on heated sections of said outer surface.

12. A material sample tube as recited in claim 11, wherein said first coating is polyimide and said organic coating is cyanoacrylate.

13. A material sample tube as recited in claim 4, comprising:
    (a) fused silica capillary having a polyimide coating on a first outer surface of said longitudinal section;
    (b) a cyanoacrylate coating on a second outer surface of said reverse bend; and
    (c) a polyester resin coating on said first and second outer surfaces.

14. A material sample tube for a spectrometer having a measurement zone, said material sample tube, comprising:
    (a) non-magnetic material, and
    (b) said non-magnetic material sample tube having a plurality of continuous and unbroken passes through said spectrometer measurement zone, wherein each pass has a longitudinal section and a reverse bend on at least one end of the longitudinal section.

15. A material sample tube as recited in claim 14, wherein the longitudinal section has a length that is sufficient to place the reverse bend outside the measurement zone.

16. A material sample tube as recited in claim 15, wherein the spectrometer is an NMR spectrometer.

* * * * *